United States Patent
Tsubota et al.

(10) Patent No.: US 7,894,575 B2
(45) Date of Patent: Feb. 22, 2011

(54) RADIATION IMAGE CAPTURING SYSTEM

(75) Inventors: Keiji Tsubota, Kanagawa (JP); Yutaka Yoshida, Kanagawa (JP); Kouichi Kitano, Kanagawa (JP); Naoyuki Nishino, Kanagawa (JP); Yasunori Ohta, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 85 days.

(21) Appl. No.: 12/534,163

(22) Filed: Aug. 3, 2009

(65) Prior Publication Data

US 2010/0078583 A1 Apr. 1, 2010

(30) Foreign Application Priority Data

Sep. 29, 2008 (JP) ............................. 2008-251030

(51) Int. Cl.
*H05G 1/38* (2006.01)
(52) U.S. Cl. ....................................................... 378/96
(58) Field of Classification Search ................... 378/62, 378/96, 98, 98.8
See application file for complete search history.

(56) References Cited

U.S. PATENT DOCUMENTS 6,801,598 B2 * 10/2004 Tashiro et al. .............. 378/98.8
2002/0186813 A1 * 12/2002 Tamura et al. .............. 378/98.8
2002/0191741 A1 * 12/2002 Brendler et al. ................ 378/96
2009/0201841 A1 * 8/2009 Tachikawa ................... 370/310

FOREIGN PATENT DOCUMENTS

JP 2008-132216 6/2008

* cited by examiner

*Primary Examiner*—Irakli Kiknadze
(74) *Attorney, Agent, or Firm*—Solaris Intellectual Property Group, PLLC (57) ABSTRACT

A radiation image capturing system is provided. A radiation source control device includes a first timing component, and a control component that, when a time of the first timing component has reached a pre-specified exposure start time, controls a radiation source, which emits radiation, and performs control to cause radiation to be irradiated for a predetermined duration from the radiation source. A radiation image capturing device includes a second timing component that measures time, which is synchronized with the first timing component, a sensor portion that generates charges in accordance with irradiation of radiation and that is irradiated with the radiation from the radiation source, and a generation component that, after a time of the second timing component has passed through the predetermined duration from the exposure start time, reads out the charges generated at the sensor portion and generates image data representing a radiation image.

13 Claims, 7 Drawing Sheets

RADIATION IMAGE CAPTURING SYSTEM

CROSS-REFERENCE TO RELATED APPLICATION

This application claims priority under 35 USC 119 from Japanese Patent Application No. 2008-251030, the disclosure of which is incorporated by reference herein.

BACKGROUND OF THE INVENTION

1. Field of the Invention

The present invention relates to a radiation image capturing system.

2. Description of the Related Art

In recent years, FPDs (flat panel detectors) have been realized in which a radiation-sensitive layer is disposed on a TFT (thin film transistor) active matrix substrate and radiation can be directly converted to digital data. Using these FPDs and the like, portable radiation image capturing devices (below referred to as electronic cassettes) have been realized that generate image information, which represents a radiation image capturing image manifested by irradiated radiation, and store the generated image information.

Because such an electronic cassette is portable, it may photograph a patient rested on a stretcher, a bed or the like, and a location of photographing may be adjusted by altering a position of the electronic cassette. Therefore, a patient who cannot be moved may be flexibly dealt with.

However, at an FPD, charges arise even in states in which X-rays are not irradiated, because of dark current and the like, and the charges are accumulated in the pixels. Therefore, a reset operation, which reads out and erases charges that have accumulated in the pixels of an FPD during waiting, is repeatedly carried out. When instruction information requesting image capturing of a radiation image is received from a control apparatus for controlling (known as a console), the reset operation corresponding to a full frame is completed before an instruction operation instructing the start of image capturing is sent to the console. When the console receives this instruction information, the console causes X-rays to be irradiated from a radiation producing device to the electronic cassette. After a predetermined duration from the sending of the instruction information, the electronic cassette performs a read-out of charges that have accumulated in the pixels of the FPD.

However, if communications between the electronic cassette and the console are wireless communications, communication conditions may become unstable and instruction information may be delayed before being received by the console. If, for example, instruction information instructing the start of image capturing is delayed, a timing at which X-rays are irradiated from the radiation producing device to the electronic cassette is delayed, and synchronization in the timing of image capturing cannot be attained.

Accordingly, Japanese Patent Application Laid-Open (JP-A) No. 2008-132216 has disclosed a technology of, at an X-ray image capturing device (an electronic cassette), performing idling driving which repeats refreshing and blank-reading of charges of an FPD at predetermined intervals, and at an X-ray control device (a console), keeping an X-ray image capturing-possible period synchronized with an opto-electronic conversion mode period of the idling driving of the image capturing device, with a timer.

However, in the technology of JP-A No. 2008-132216, the electronic cassette simply repeats the same idling driving, and cannot deal with different image capturing modes in which the X-ray image capturing-possible period is altered. Moreover, in the technology of JP-A No. 2008-132216, if synchronization of the X-ray image capturing-possible period of the console with the electronic cassette is lost due to a single occurrence of image capturing in a different image capturing mode or a malfunction or the like, it becomes impossible to synchronize the image capturing timings. Further yet, in the technology of JP-A No. 2008-132216, if there are plural electronic cassettes, it is necessary to keep X-ray image capturing-possible periods for the plural electronic cassettes synchronized at the console.

SUMMARY OF THE INVENTION

The present invention has been made in view of the aforementioned situation and an object is to provide a radiation image capturing system capable of synchronizing image capturing timings and assuredly photographing radiation images.

According to an aspect of the invention, there is provided a radiation image capturing system including: a radiation source control device including a first timing component that measures time, and a control component that, when a time of the first timing component has reached a pre-specified exposure start time, controls a radiation source, which emits radiation, and performs control to cause radiation to be irradiated for a predetermined duration from the radiation source; and a radiation image capturing device including a second timing component that measures time, which is synchronized with the first timing component, a sensor portion that generates charges in accordance with irradiation of radiation and that is irradiated with the radiation from the radiation source, and a generation component that, after a time of the second timing component has passed through the predetermined duration from the exposure start time, reads out the charges generated at the sensor portion and generates image data representing a radiation image.

DETAILED DESCRIPTION OF THE INVENTION

Herebelow, the best exemplary embodiment for carrying out the present invention will be described in detail with reference to the drawings.

Firstly, the constitution of a radiology information system 10 relating to the exemplary embodiment will be described.

Figure 1:
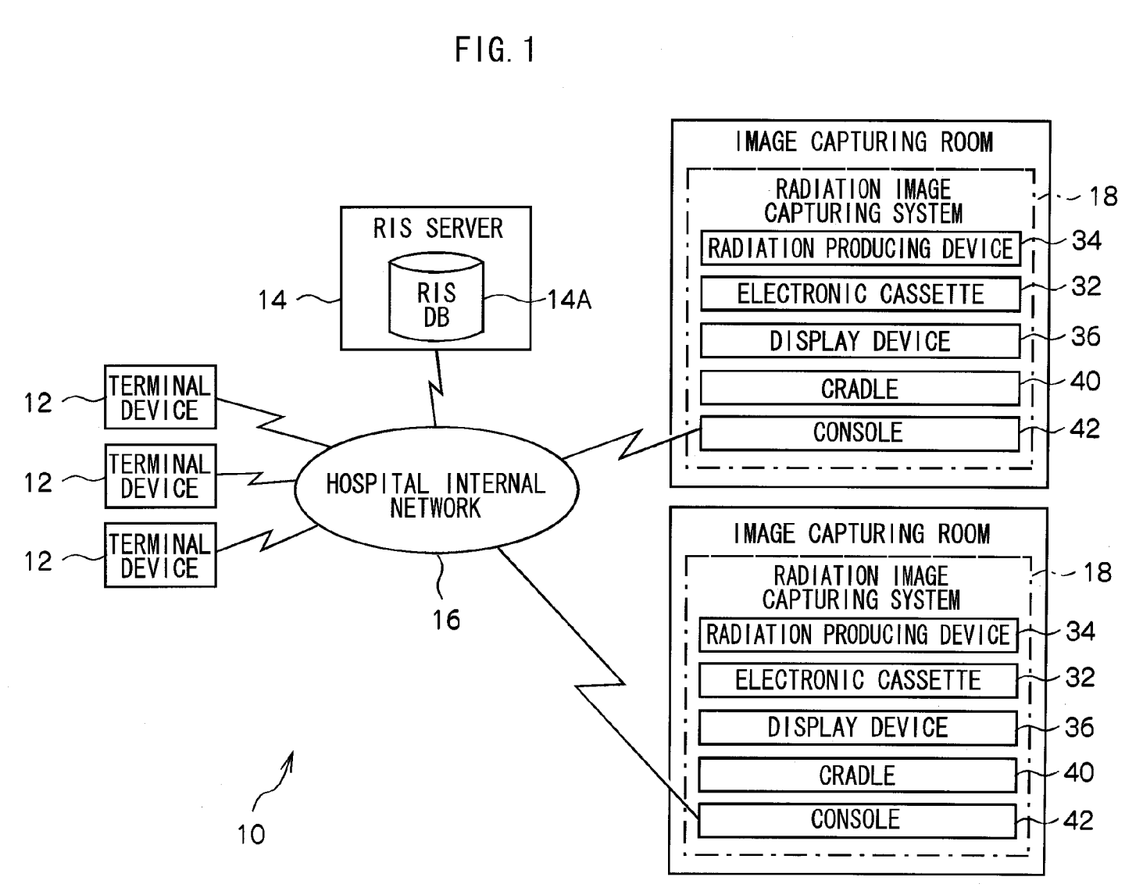
FIG. 1 is a block diagram illustrating structure of a radiology information system relating to an exemplary embodiment.

FIG. 1 shows a block diagram illustrating structural elements of the radiology information system 10 relating to the present exemplary embodiment (below referred to as the RIS 10, RIS standing for radiology information system).

The RIS 10 is a system for carrying out information management of clinical appointments, clinical records and so forth in a radiology department, and constitutes a portion of a hospital information system (HIS).

The RIS 10 is constituted with a plurality of image capturing request terminal devices 12 (below referred to as terminal devices 12), an RIS server 14, and a radiation image capturing system 18 being connected to a hospital internal network 16, which is formed with a wired or wireless LAN (local area network). The radiation image capturing system 18 is disposed in individual radiography rooms (or operating rooms) in the hospital. Herein, the RIS 10 constitutes a portion of a hospital information system (HIS) provided in the same hospital, and an HIS server (not illustrated) that administers the whole of the HIS is also connected to the hospital internal network 16.

Each terminal device 12 is for a doctor 26 (see FIG. 2), a radiographer or the like to input and monitor clinical information, equipment bookings and the like. Image capturing requests (image capturing bookings) for radiation images are also conducted from the terminal device 12. The terminal device 12 is constituted by a personal computer with a display device and is connected with the RIS server 14 by the hospital internal network 16, enabling communication therebetween.

The RIS server 14 receives image capturing requests from the terminal devices 12 and manages an image capturing schedule for radiation images at the radiation image capturing system 18. The RIS server 14 is constituted to include a database 14A.

The database 14A is constituted to include: information relating to patients 30, such as information on attributes of each patient 30 (see FIG. 2) (name, gender, date of birth, age, blood type, a patient ID number and the like), medical history, treatment history, previously photographed radiation images, and the like; information relating to electronic cassettes 32 of the radiation image capturing system 18, such as an identification number of each electronic cassette 32 and type, size, sensitivity, applicable locations of image capturing (details of image capturing requests that can be handled), the date of first use, the number of uses, and the like; and environmental information representing environments in which the electronic cassettes 32 are used to photograph radiation images, which is to say environments in which the electronic cassettes 32 are employed (for example, an operating room, an image capturing room specially equipped for image capturing of radiation images, or the like).

The radiation image capturing system 18 carries out image capturing of radiation images in accordance with control by the doctor 26, a radiographer or the like, in response to instructions from the RIS server 14. The radiation image capturing system 18 is provided with a radiation producing device 34, the electronic cassette 32, a display device 36, a cradle 40, and a console 42. The radiation producing device 34 irradiates radiation X, constituted with radiation amounts depending on image capturing conditions, at a subject of photographing. The electronic cassette 32 incorporates a radiation detector 60 (see FIG. 3) that detects the radiation X that has passed through the patient 30 and converts the radiation X to radiation image information. The display device 36 displays a radiation image based on the radiation X detected by the radiation detector 60. The cradle 40 charges a battery incorporated in the electronic cassette 32. The console 42 controls the electronic cassette 32, the radiation producing device 34, the display device 36 and the cradle 40.

Figure 2:
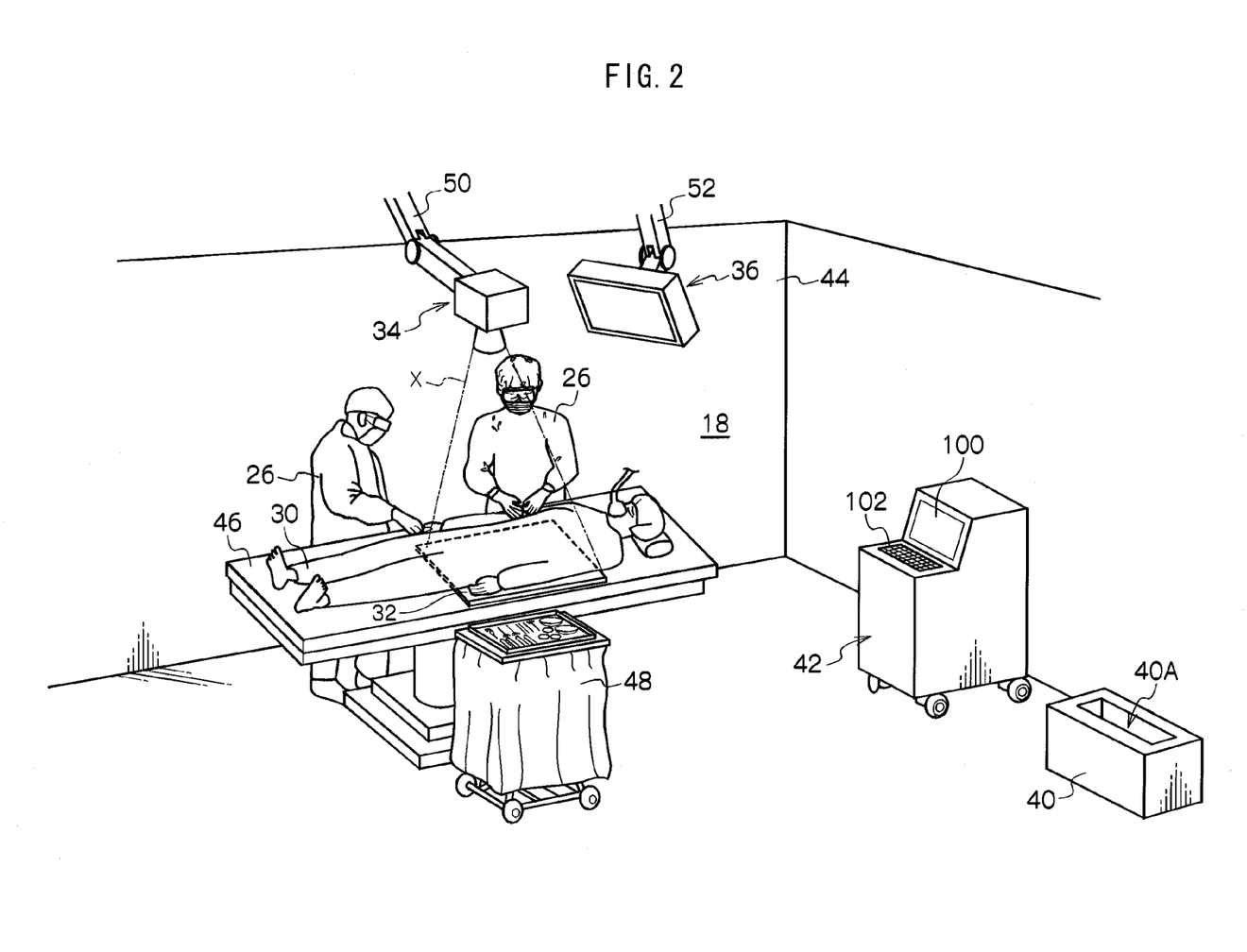
FIG. 2 is a view illustrating conditions in an operating room in which a radiation image capturing system relating to the exemplary embodiment is disposed.

FIG. 2 illustrates conditions in which the radiation image capturing system 18 relating to the present exemplary embodiment is disposed, for example, conditions in which the radiation image capturing system 18 is disposed in an operating room 44 that serves as an image capturing room. In the radiation image capturing system 18 relating to the present exemplary embodiment, the radiation producing device 34 and the display device 36 are respectively connected with the console 42 by cables, and perform exchanges of various kinds of information by wired communications. The cables connecting between the equipment are not shown in FIG. 2. Exchanges of various kinds of information are also performed between the electronic cassette 32 and the console 42, by wireless communications.

In the operating room 44 of FIG. 2, in addition to the radiation image capturing system 18, an operating table 46 is provided and an instrument table 48 is disposed beside the operating table 46. The patient 30 is laid down on the operating table 46, and various instruments to be used in surgery by the doctor 26 are placed on the instrument table 48. Various pieces of equipment required for surgery are disposed around the operating table 46, such as anesthetic equipment, suction equipment, an electrocardiograph, a sphygmomanometer and the like. These devices are not illustrated in FIG. 2).

The radiation producing device 34 is coupled to an adjustable arm 50 and is movable to a desired position corresponding with a location of photographing of the patient 30. The radiation producing device 34 is also retractable to a position that will not interfere with surgery by the doctor 26. Similarly, the display device 36 is coupled to an adjustable arm 52 and is movable to a position at which the doctor 26 can easily check photographed radiation images.

The cradle 40 is formed with an accommodation portion 40A capable of accommodating the electronic cassette 32.

The electronic cassette 32 is accommodated in the accommodation portion 40A of the cradle 40 when on standby, and charging of the incorporated battery is implemented. At a time of image capturing of a radiation image, the electronic cassette 32 is removed from the cradle 40 and disposed at a location of photographing of the patient 30.

Herein, the electronic cassette 32 is not limited to cases of use in the operating room 44. For example, the electronic cassette 32 may also be applied to check-ups, hospital rounds and the like.

Figure 3:
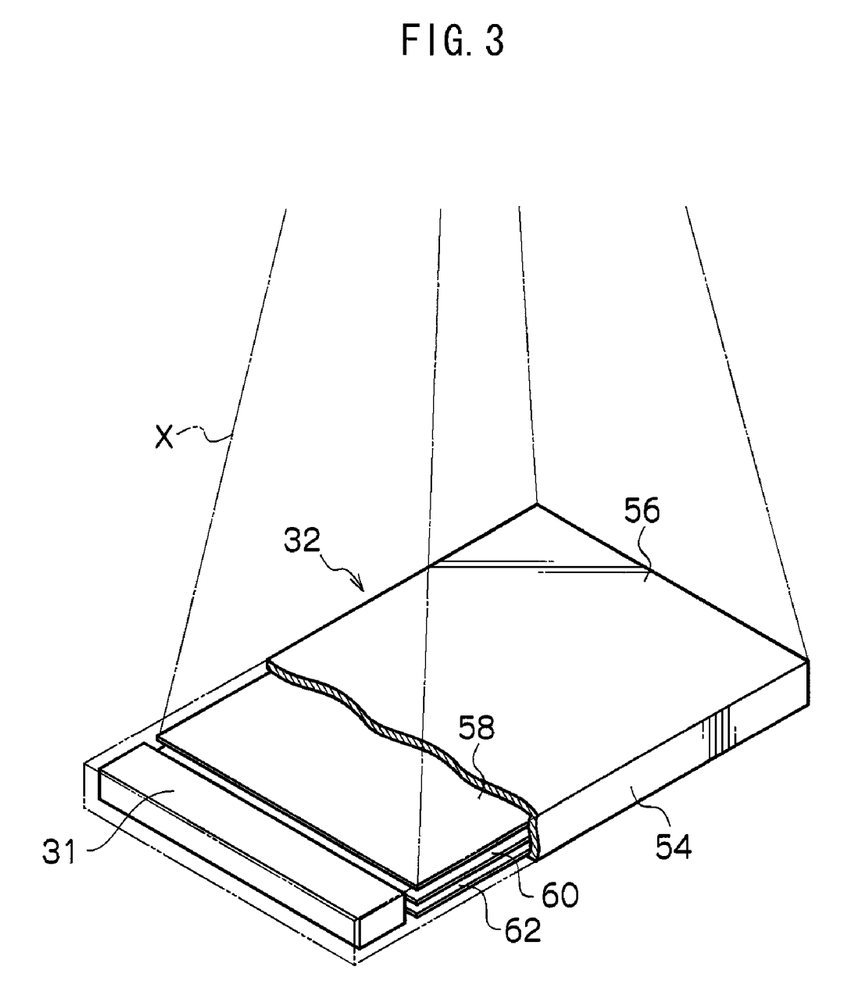
FIG. 3 is a transparent perspective view illustrating internal structure of an electronic cassette relating to the exemplary embodiment.

FIG. 3 illustrates internal structure of the electronic cassette 32 relating to the exemplary embodiment.

As shown in FIG. 3, the electronic cassette 32 is provided with a housing 54, which is formed of a material that transmits the radiation X and is structured to be waterproof and tightly sealed. During use in the operating room 44 or the like, blood and other microorganism contaminants and the like may adhere to the electronic cassette 32. Therefore, the electronic cassette 32 is structured to be waterproof and tightly sealed, and is washed with disinfectant as necessary. Thus, the individual electronic cassettes 32 may be repeatedly used.

Inside the housing 54, a grid 58, the radiation detector 60 and a lead plate 62 are arranged in this order from the side of an irradiation surface 56 of the housing 54 onto which the radiation X is irradiated. The grid 58 eliminates scattered rays of the radiation X caused by the patient 30. The radiation detector 60 detects the radiation X that has passed through the patient 30. The lead plate 62 absorbs back-scattered rays of the radiation X. Herein, the irradiation surface 56 of the housing 54 may be constituted as the grid 58.

A case 31 that accommodates electronic circuits, including a microcomputer, and a rechargeable secondary cell is disposed at one end of the interior of the housing 54. The radiation detector 60 and the electronic circuits are operated by electrical power supplied from the secondary cell accommodated in the case 31. In order to prevent the various circuits accommodated inside the case 31 being damaged due to irradiation of the radiation X, it is desirable for a shielding member of lead plating or the like to be disposed at the irradiation surface 56 side of the case 31.

Figure 4:
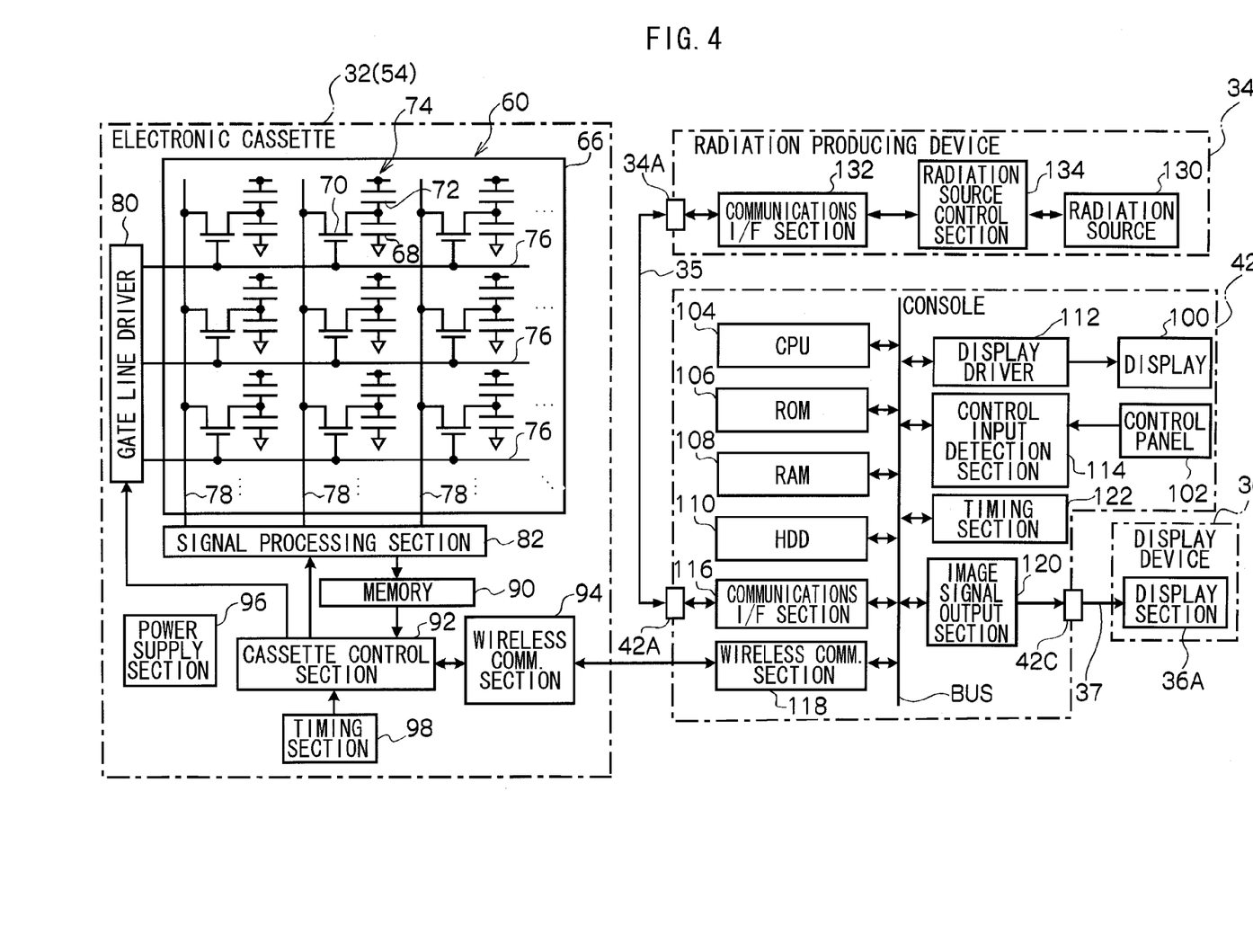
FIG. 4 is a block diagram illustrating detailed structure of the radiation image capturing system relating to the exemplary embodiment.

FIG. 4 shows a block diagram illustrating detailed structure of the radiation image capturing system 18 relating to the exemplary embodiment.

At the radiation producing device 34, a connection terminal 34A for carrying out communications with the console 42 is provided. At the console 42, a connection terminal 42A, for carrying out communications with the radiation producing device 34, and a connection terminal 42C, for outputting image signals to the display device 36, are provided.

The radiation producing device 34 is connected to the console 42 via a communications cable 35. The display device 36 is connected to the console 42 via a communications cable 37.

The radiation detector 60 incorporated into the electronic cassette 32 is structured by an optoelectronic conversion layer, which absorbs the radiation X and converts the same to electric charges, being layered onto a TFT active matrix substrate 66. The optoelectronic conversion layer is formed of, for example, noncrystalline a-Se (amorphous selenium) of which selenium is a principal component (for example, a proportional content of at least 50%). When the radiation X is irradiated thereon, the optoelectronic conversion layer generates electric charges (electron-hole pairs) thereinside with charge amounts corresponding to irradiated radiation amounts. Thus, the irradiated radiation X is converted to electric charges. Here, instead of a radiation-to-charge conversion material such as amorphous selenium that converts the radiation X directly to electric charges, the radiation detector 60 may indirectly convert to electric charges using a fluorescent material and optoelectronic conversion elements (photodiodes). As fluorescent materials, gadolinium sulfate (GOS), cesium iodide (CsI) and the like are well known. In such a case, a radiation X-to-light conversion is performed by the fluorescent material, and a light-to-electric charge conversion is carried out by photodiodes of the optoelectronic conversion elements.

Cumulative capacitors 68, which accumulate the charges generated in the optoelectronic conversion layer, and pixel portions 74, which are provided with TFTs 70 for read-out of the charges accumulated in the cumulative capacitors 68, are numerously provided in a matrix form on the TFT active matrix substrate 66 (the optoelectronic conversion layer corresponding with each of the pixel portions 74 is schematically shown as an optoelectronic conversion portion 72 in FIG. 4). The charges that are generated in the optoelectronic conversion layer in accordance with irradiation of the radiation X onto the electronic cassette 32 are accumulated in the individual cumulative capacitors 68 of the pixel portions 74. Thus, the image information carried by the radiation X irradiated onto the electronic cassette 32 is converted to electric charge information and retained in the radiation detector 60.

Plural gate lines 76 and plural data lines 78 are provided in the TFT active matrix substrate 66. The gate lines 76 extend in a certain direction (a column direction) and are for turning the TFTs 70 of the pixel portions 74 on and off. The data lines 78 are provided in a direction crossing the gate lines 76 (a row direction) and are for reading out the accumulated charges from the cumulative capacitors 68 via the TFTs 70 that have been turned on. The respective gate lines 76 are connected to a gate line driver 80, and the respective data lines 78 are connected to a signal processing section 82. When charges are accumulated in the cumulative capacitors 68 of the respective pixel portions 74, the TFTs 70 of the pixel portions 74 are turned on sequentially, column by column, by signals provided through the gate lines 76 from the gate line driver 80. The charges accumulated in the cumulative capacitors 68 of the pixel portions 74 for which the TFTs 70 have been turned on are transferred through the data lines 78 as charge signals and inputted to the signal processing section 82. Thus, the charges accumulated in the cumulative capacitors 68 of the respective pixel portions 74 are sequentially read out in column units.

Figure 5:
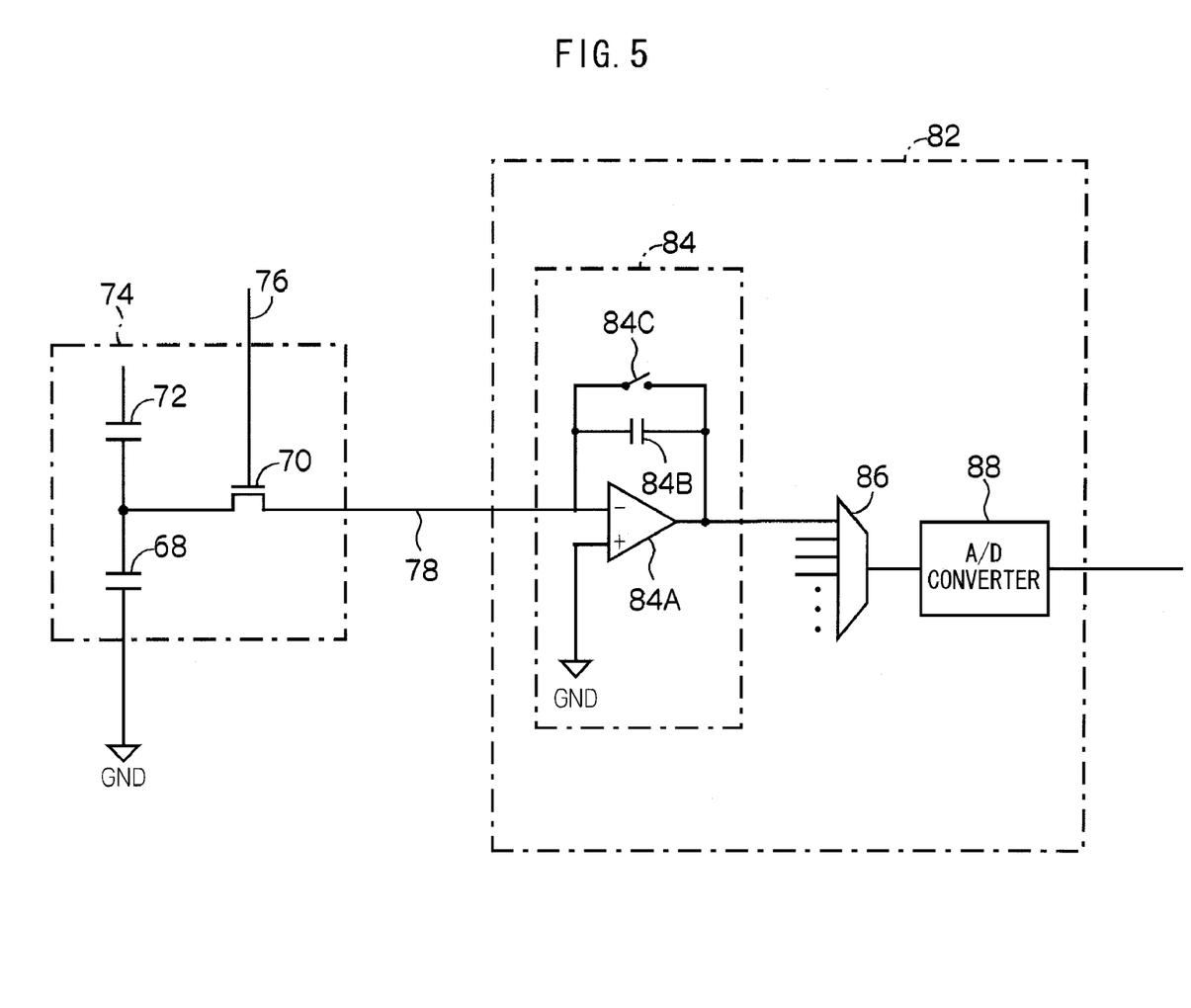
FIG. 5 is an equivalent circuit diagram concerning a single-pixel portion of a radiation detector relating to the exemplary embodiment.

FIG. 5 shows an equivalent circuit diagram concerning a single-pixel portion of the radiation detector 60 relating to the present exemplary embodiment.

As shown in FIG. 5, the source of the TFT 70 is connected to the data line 78, and the data line 78 is connected to the signal processing section 82. The drain of the TFT 70 is connected to the cumulative capacitor 68 and the optoelectronic conversion portion 72, and the gate of the TFT 70 is connected to the gate line 76.

The signal processing section 82 is provided with a sample and hold circuit 84 for each data line 78. The charge signals transferred through the data lines 78 are retained at the respective sample and hold circuits 84. The sample and hold circuit 84 is structured to include an op amp 84A and a capacitor 84B, and converts charge signals to analog voltages. The sample and hold circuit 84 is further provided with a switch 84C, which serves as a reset circuit that shorts together the two electrodes of the capacitor 84B and discharges charge accumulated in the capacitor 84B.

A multiplexer 86 and an A/D converter 88 are connected, in this order, to the output side of the sample and hold circuit 84. The charge signals retained by the respective sample and hold circuits are converted to analog voltages, sequentially (serially) inputted into the multiplexers 86, and converted to digital image data by the A/D converters 88.

A memory 90 is connected to the signal processing section 82 (see FIG. 4), and the image information outputted from the A/D converters 88 of the signal processing section 82 is sequentially stored in the memory 90. The memory 90 has a storage capacity capable of storing a predetermined number of frames of image information representing radiation images. Each time reading of charges for one line is carried out, image information corresponding to the one line that is read out is sequentially stored in the memory 90.

The memory 90 is connected with a cassette control section 92 that controls operations of the electronic cassette 32 as a whole. The cassette control section 92 is realized by a microcomputer, and a wireless communications section 94 is connected to the cassette control section 92. The wireless communications section 94 complies with wireless LAN (local area network) standards, as represented by IEEE (Institute of Electrical and Electronics engineers) 802.11a/b/g and the like. The wireless communications section 94 controls transfers of various kinds of information between the cassette control section 92 and external equipment by wireless communications. The cassette control section 92 is capable of wireless communications with the console 42 via the wireless communications section 94, and may exchange various kinds of information with the console 42. The cassette control section 92 stores later-described image capturing control information which is received from the console 42, and starts a read-out of charges in accordance with this information.

A timing section 98 that measures time is connected to the cassette control section 92. The timing section 98 features a radio clock function and, when reference electromagnetic signals representing a reference time are received from an external transmitter, performs time correction. The cassette control section 92 may ascertain a current time by obtaining time information from the timing section 98.

The electronic cassette 32 is also provided with a power supply section 96. The various circuits and elements mentioned above (the gate line driver 80, the signal processing section 82, the memory 90, the wireless communications section 94, the microcomputer that functions as the cassette control section 92, the timing section 98 and the like) are driven by electrical power supplied from the power supply section 96. The power supply section 96 incorporates a battery (a rechargeable secondary cell), so as not to impede portability of the electronic cassette 32, and provides power to the various circuits and elements from the charged battery.

Meanwhile, the console 42 is structured to serve as a server computer. The console 42 is provided with a display 100, which displays control menus, photographed radiation images and the like, and a control panel 102, which is structured to include plural keys and at which various kinds of information and control instructions are inputted.

The console 42 relating to the present exemplary embodiment is provided with: a CPU 104 that administers operations of the device as a whole; a ROM 106 at which various programs, including a control program, and the like are stored in advance; a RAM 108 that temporarily stores various kinds of data; an HDD (hard disc drive) 110 that stores and retains various kinds of data; a display driver 112 that controls displays of various kinds of information at the display 100; a control input detection section 114 that detects control conditions at the control panel 102; a communications interface (I/F) section 116 that is connected to the connection terminal 42A and carries out exchanges of various kinds of information, such as exposure conditions, information on the state of the radiation producing device 34 and the like, with the radiation producing device 34 via the connection terminal 42A and the communications cable 35; a wireless communications section 118 that carries out exchanges of various kinds of information, such as image capturing control information, image information and the like, with the electronic cassette 32 by wireless communications; an image signal output section 120 that is connected to the connection terminal 42C and outputs image information to the display device 36 via the connection terminal 42C and the communications cable 37; and a timing section 122 that measures time.

Similarly to the timing section 98, the timing section 122 features a radio clock function and performs time corrections when reference electromagnetic signals are received.

The CPU 104, the ROM 106, the RAM 108, the HDD 110, the display driver 112, the control input detection section 114, the communications I/F section 116, the wireless communications section 118, the image signal output section 120 and the timing section 122 are connected to one another by a system bus. Thus, the CPU 104 may implement access to the ROM 106, the RAM 108 and the HDD 110, and may implement each of control of display of various kinds of information at the display 100 via the display driver 112, control of exchanges of various kinds of information with the radiation producing device 34 via the communications I/F section 116, control of exchanges of various kinds of information with the electronic cassette 32 via the wireless communications section 118, and control of images displayed at the display device 36 via the image signal output section 120. The CPU 104 may also acquire states of control by users from the control panel 102 via the control input detection section 114, and the CPU 104 may acquire current times by obtaining time information from the timing section 122.

The radiation producing device 34 is provided with a radiation source 130 that outputs the radiation X, a communications I/F section 132, and a radiation source control section 134. The communications I/F section 132 exchanges various kinds of information, such as exposure conditions, information on the state of the radiation producing device 34 and the like, with the console 42. The radiation source control section 134 controls the radiation source 130 on the basis of the received exposure conditions. The radiation source control section 134 is realized by a microcomputer, stores the received exposure conditions, and causes the radiation X to be irradiated from the radiation source 130 in accordance with the stored exposure conditions.

The display device 36 is provided with a display section 36A that displays images represented by received image signals.

In the present exemplary embodiment, visible displays are implemented using LCDs (liquid crystal displays) as the display device 36 and the display 100, but this is not a limitation. Visible displays may be implemented using other displays as the display section 36A and the display 100, such as organic electroluminescent displays, CRT displays and the like.

Next, overall operations of the RIS 10 relating to the present exemplary embodiment will be briefly described.

The terminal device 12 (see FIG. 1) receives an image capturing request including environment information from the doctor 26 or a radiographer. The image capturing request specifies the environment in which the electronic cassette 32 is to be used, a time/date of image capturing, and image capturing conditions (a location, angle and number of frames of image capturing, a tube voltage, tube current and irradiation duration for irradiating the radiation X, a size and sensitivity of the electronic cassette 32, and suchlike).

The terminal device 12 reports details of the received image capturing request to the RIS server 14. The RIS server 14 stores the details of the image capturing request reported from the terminal device 12 in the database 14A.

The console 42, by accessing the RIS server 14, acquires details of the image capturing request and associated environment information from the RIS server 14, and displays details of the image capturing request at the display 100 (see FIG. 2 and FIG. 4).

The radiation image capturing system 18 relating to the present exemplary embodiment features, as categories of image capturing, plural image capturing modes, such as: usual image capturing, in which a single still radiation image is photographed in response to one image capturing instruction; analog tomography, in which slice images are acquired by single photographs with one or both of the radiation producing device and the radiation detector being scanned; tomosynthesis image capturing, which produces a slice image at an arbitrary depth from a plurality of radiation images obtained by a cycle of slice scanning; video image capturing, which acquires video images; strip image capturing, which synthesizes plural radiation images to produce a strip image; and the like. Tube voltage, tube current and irradiation duration, which are exposure conditions, are specified in accordance with a quantity of radiation to be irradiated from the radiation source, a location that is the object of image capturing, and the image capturing mode. For example, in the ordinary image capturing mode which photographs still radiation images, the irradiation duration is altered between, for example, 34 ms and 1300 ms in accordance with the location of photographing, being set longer in a case in which the location of photographing is at a thicker portion of the body through which radiation is harder to transmit, and shorter in a case in which the location of photographing is a chest area that includes the moving heart. In a case in the analog tomography mode, the irradiation duration is set longer at, for example, 2300 ms.

The doctor 26, radiographer or the like starts image capturing of radiation images on the basis of the details of the image capturing request displayed at the display 100.

For example, when image capturing of a radiation image of an affected area of the patient 30 reclining on the operating table 46 as shown in FIG. 2 is to be carried out, the doctor 26, radiographer or the like disposes the electronic cassette 32 between the affected area of the patient 30 and the operating table 46 in accordance with the location and angle of image capturing, and disposes the radiation producing device 34 above the affected area. The doctor 26, radiographer or the like carries out exposure condition setting operations at the control panel 102 of the console 42 to set the exposure conditions, such as the tube voltage, tube current, irradiation duration and the like when the radiation X is irradiated, in accordance with the image capturing location of the patient 30 and image capturing conditions. When exposure preparation of the radiation producing device 34 is complete, the doctor 26, radiographer or the like performs an image capturing instruction operation at the control panel 102 of the console 42 to instruct the image capturing.

Next, operation of the radiation image capturing system 18 relating to the present exemplary embodiment will be described in detail.

Figure 6:
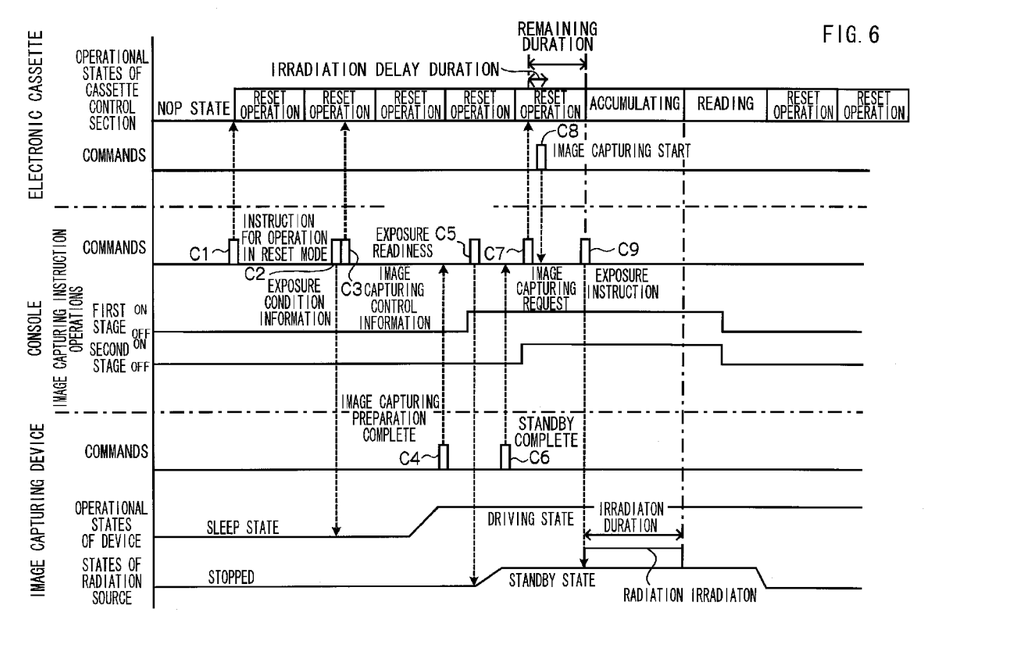
FIG. 6 is a timing chart illustrating flow of processing when a radiation image is photographed, relating to the exemplary embodiment.

FIG. 6 shows a timing chart illustrating a flow of processing when a radiation image is photographed by the radiation image capturing system 18 relating to the present exemplary embodiment.

In a state when the power supply has been turned on (a start-up state), an operation mode of the electronic cassette 32 is a non-operation state (an NOP state), which is an initial state. The electronic cassette 32 operates on the basis of instruction information received by wireless communications from the console 42.

Now, when the power supply of the electronic cassette 32 has been turned on, the radiation detector 60 incorporated in the electronic cassette 32 (see FIG. 4) accumulates charges in the cumulative capacitors 68 even when the radiation X is not being irradiated, because of dark current and the like. Accordingly, when the operation mode is in the non-operation state, the cassette control section 92 outputs instruction signals instructing resets to the signal processing section 82. When an instruction signal instructing a reset is inputted to the signal processing section 82, the switch 84C (see FIG. 5) turns on and the two electrodes of the capacitor 84B are shorted together. Thus, unnecessary accumulated charge at the capacitor 84B is discharged by the two electrodes of the capacitor 84B being shorted together.

When the electronic cassette 32 becomes capable of communication, the console 42 sends instruction information C1, instructing operation in a reset mode, to the electronic cassette 32 by wireless communications.

When the cassette control section 92 receives the instruction information C1 instructing operation in the reset mode, the operation mode thereof switches into the reset mode, the cassette control section 92 controls the gate line driver 80, ON signals are outputted from the gate line driver 80 to the gate lines 76 line by line, and the TFTs 70 connected to the gate lines 76 are turned on line by line. As a result, the charges accumulated at the cumulative capacitors 68 flow out into the data lines 78 as charge signals, line by line. While the operation mode is in the reset mode, the cassette control section 92 outputs ON signals to the gate lines 76 line by line and repeats the reset operation to reset the charges accumulated in the cumulative capacitors 68 in amounts corresponding to a full frame.

When exposure condition setting operations are carried out at the control panel 102, the console 42 sends exposure condition information C2, of the tube voltage, tube current, irradiation duration and the like specified by the exposure condition setting operations, to the radiation producing device 34 via the communications cable 35. The console 42 also sends image capturing control information C3, such as an irradiation duration for which the radiation is to be irradiated from the radiation producing device 34 at the time of image capturing and the like, to the electronic cassette 32 by wireless communications.

When a power supply of the radiation producing device 34 is turned on and predetermined start-up operations have ended, the operation state of the radiation producing device 34 goes into a sleep state and stands by. When the exposure condition information C2 is received, the radiation producing device 34 stores the received exposure condition information and the operation state switches into a driving state. When the operation state has returned to the driving state, the radiation producing device 34 sends information C4, representing the completion of image capturing preparation, to the console 42 via the communications cable 35.

When the cassette control section 92 of the electronic cassette 32 receives the image capturing control information C3, the cassette control section 92 stores the received image capturing control information.

When the console 42 receives the information C4 representing the completion of image capturing preparation, the console 42 displays the fact that image capturing preparation is complete at the display 100, and the image capturing instruction operation that instructs image capturing is enabled at the control panel 102. In the radiation image capturing system 18 relating to the present exemplary embodiment, the image capturing instruction operation at the control panel 102 is a two-stage operation. A first stage image capturing instruction operation is carried out at the control panel 102, after which a second stage image capturing operation instruction operation is carried out, and hence image capturing of a radiation image is performed. This two-stage image capturing instruction operation may be, for example, pressing two buttons of the control panel 102 one after another, or may be, for example half-pressing and then fully pressing a single button.

When the first stage image capturing instruction operation is carried out at the control panel 102, the console 42 sends instruction information C5, representing exposure readiness, to the radiation producing device 34 via the communications cable 35.

When the radiation producing device 34 receives the instruction information C5 representing exposure readiness, the radiation source 130 is put on standby so as to carry out exposure with the tube voltage and tube current represented by the most recently stored exposure condition information. When standing by of the radiation source 130 is complete, the radiation producing device 34 sends information C6, representing standby completion, to the console 42 via the communications cable 35.

When the console 42 receives the information C6 representing standby completion, the second stage image capturing instruction operation is enabled. When the second stage image capturing instruction operation is carried out at the control panel 102, the console 42 sends instruction information C7, requesting image capturing, to the electronic cassette 32 by wireless communications.

When the cassette control section 92 receives the instruction information C7 requesting image capturing, the cassette control section 92 carries out the following exposure timing determination processing, which determines the timing of exposure.

Figure 7:
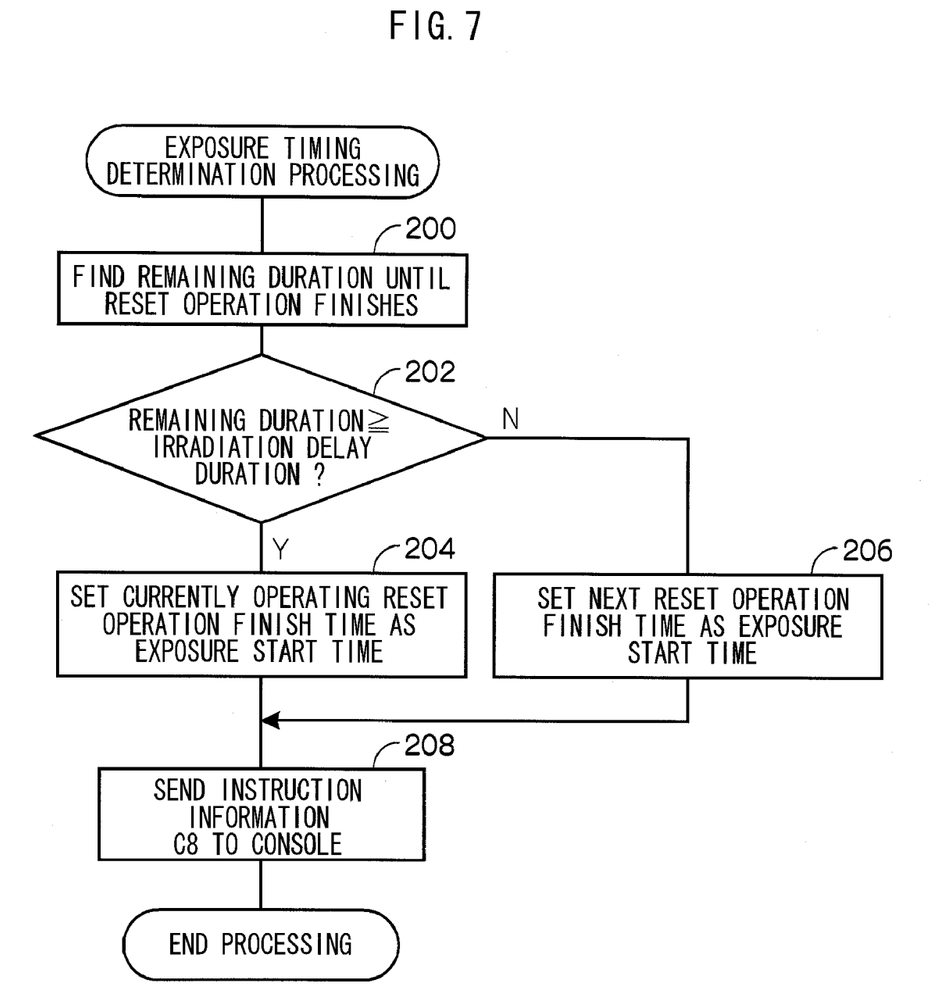
FIG. 7 is a flowchart illustrating a flow of exposure timing determination processing relating to the exemplary embodiment.

FIG. 7 shows a flowchart illustrating flow of the exposure timing determination processing. A program of this exposure timing determination processing is stored in advance in a predetermined region of a storage section (not illustrated) such as a ROM or the like that is provided at the cassette control section 92.

In step 200 of FIG. 7, a duration remaining until completion of a reset operation corresponding to a full frame is found, on the basis of which of the gate lines 76 the gate line driver 80 is outputting ON signals to at the time when the instruction information C7 requesting image capturing is received.

Then, in step 202, it is judged whether or not the remaining duration that has been found in step 200 is greater than a predetermined irradiation delay duration, which is required from when a start of irradiation is instructed until the radiation is actually irradiated. If this judgment is positive, the processing advances to step 204, and if the judgment is negative, the processing advances to step 206.

In the radiation image capturing system 18 relating to the present exemplary embodiment, irradiation of radiation is enabled at the electronic cassette 32 and there is a time lag before the radiation is actually irradiated at the electronic cassette 32 from the radiation producing device 34. Therefore, for the present exemplary embodiment, a duration from irradiation of radiation being enabled at the electronic cassette 32 until the irradiation is actually irradiated is measured, by experiment or the like, and the irradiation delay duration is specified as a duration corresponding to the duration from the irradiation of radiation being allowed until the radiation is actually irradiated.

In step 204, a time at which the reset operation corresponding to a full frame that is currently operating will finish is set as an exposure start time. Alternatively, in step 206, a time at which the next reset operation corresponding to a full frame will finish is set as the exposure start time.

Then, in step 208, instruction information C8 instructing the start of image capturing, which includes exposure information indicating the set exposure start time, is sent to the console 42 by wireless communications, and the processing ends.

Thus, as shown in the example in FIG. 6, if the remaining duration until the reset operation currently operating will be complete is above the irradiation delay duration, the time at which the currently operating reset operation finishes is the exposure start time.

When the console 42 receives either kind of the instruction information C8 instructing the start of image capturing, the console 42 waits until the exposure start time indicated by the exposure information included in the instruction information C8. When the exposure start time is reached, the console 42 sends instruction information C9, instructing exposure, to the radiation producing device 34 via the communications cable 35.

When the radiation producing device 34 receives the instruction information C9 instructing exposure, the radiation producing device 34 causes the radiation X to be irradiated from the radiation source 130 for the irradiation duration represented by the most recently stored exposure condition information.

The radiation X that is irradiated from the radiation source 130 reaches the electronic cassette 32 after passing through the patient 30. Hence, charges according to radiation quantities of the irradiated radiation X are accumulated in the cumulative capacitors 68 of the pixel portions 74 of the radiation detector 60 incorporated in the electronic cassette 32.

The cassette control section 92 performs the reset operation until the reset operation is complete. When the reset operation corresponding to the full frame is complete, the cassette control section 92 switches the operation mode into the image capturing mode. The time at which the reset operation corresponding to the full frame finishes is the exposure start time. When the cassette control section 92 enters the image capturing mode, the cassette control section 92 waits for the exposure duration, which is stored as image capturing control information, and then controls the gate line driver 80, causing ON signals to be outputted to the gate lines 76 from the gate line driver 80 line by line and causing the TFTs 70 connected to the gate lines 76 to be turned on line by line. Thus, reading is started after the exposure duration from the exposure start time. Therefore, the duration of accumulation charges in the pixel portions 74 of the radiation detector 60 and the exposure duration for which the radiation X is irradiated from the radiation source 130 can be made to match, and there is no need to wait excessively while charges are accumulating. Thus, amounts of noise may be reduced.

When the radiation detector 60 turns on the TFTs 70 connected to the gate lines 76 line by line, the charges accumulated in the cumulative capacitors 68 flow out into the respective data lines 78 as charge signals, line by line. The charge signals that have flowed out into the data lines 78 are inputted into the individual sample and hold circuits 84 and converted to voltage signals, and the converted voltage signals are sequentially (serially) inputted into the multiplexers, converted to digital image information by the A/D converters, and stored in the memory 90.

When the cassette control section 92 finishes reading out the image information corresponding to the full frame (one frame), the cassette control section 92 switches the operation mode thereof into the reset mode. The cassette control section 92 switches into the reset mode because continuous image capturing is not being performed in this case; however, continuous image capturing may also be performed.

When the irradiation of the radiation X from the radiation source 130 finishes, the console 42 sends an image information transfer request signal to the electronic cassette 32 by wireless communications.

When the cassette control section 92 receives the image information transfer request signal, the cassette control section 92 sends the image information stored in the memory 90 to the console 42 one frame at a time.

At the console 42, predetermined image processing is applied to the image information corresponding to one frame, and the image-processed image information is stored in the HDD 110, having been associated with the patient information of the patient 30. The console 42 also outputs image signals representing the image-processed radiation image to the display device 36, and the radiation image is displayed at the display section 36A of the display device 36. The doctor 26 conducts surgery while checking the radiation image displayed at the display section 36A.

As described hereabove, according to the present exemplary embodiment, the timing section 122 which measures time is provided at the console 42, and the timing section 98 which measures time synchronously with the timing section 122 is provided at the electronic cassette 32, and these respectively measure time. At the console 42, when a pre-specified exposure start time is reached, radiation is irradiated for a predetermined duration from the radiation source 130. At the electronic cassette 32, after the predetermined duration has passed from the exposure start time, charges generated in the radiation detector 60 are read out and image data representing a radiation image is generated. Thus, image capturing timings may be synchronized and radiation images may be assuredly photographed.

Further, according to the present exemplary embodiment, because times at the console 42 and the electronic cassette 32 are synchronized, different image capturing modes in which irradiation durations of X-rays are altered may be dealt with ease.

In the present exemplary embodiment, a case has been described in which the radiation image capturing system 18 is provided with one each of the console 42 and the electronic cassette 32. However, the console 42 and/or the electronic cassette 32 may be plurally provided. According to the present exemplary embodiment, even if the console 42 and/or the electronic cassette 32 are plurally provided, the times are synchronized. Therefore, if, for example, there are plural electronic cassettes, there is no need to retain parameters of image capturing mode information, time offsets and the like of the electronic cassettes at the console each time an electronic cassette is added; it is sufficient just to report an exposure time (a start time or both start and finish times) to any electronic cassette. Moreover, even when a new console that is to communicate with the electronic cassette(s) is added, the old and new consoles and electronic cassette simply acquire synchronization to the same time (for example, a time matched with a radio clock). Consequently, because the new console and the electronic cassette are synchronized, there is no problem such as synchronization with the console being shifted from previously, and timing management at the console 42 is made simple.

In the exemplary embodiment described above, a case of application to the electronic cassette 32, which is a portable radiation image capturing device, has been described. However, the present invention is not limited thus and may be applied to a stationary radiation image capturing device.

Further, in the above exemplary embodiment, a case has been described in which the timing section 98 and the timing section 122 have radio clock functions, receiving reference signals transmitted from a transmitter and performing time corrections. However, the present invention is not limited thus. For example, times may be corrected by receiving and using time information included in electromagnetic waves transmitted from GPS satellites, time information included in electromagnetic control signals transmitted from base stations for portable telephones, time signals on television or radio, or the like. As a further example, the time of either of the console 42 and the electronic cassette 32 may serve as a reference and synchronization carried out to the local time.

In the above exemplary embodiments, a case has been described in which the exposure start time is sent from the electronic cassette 32 to the console 42. However the present invention is not limited thus. For example, the exposure start time may be sent from the console 42 to the electronic cassette 32. For such a case it is sufficient that the cassette control section 92 controls the reset operation such that the reset operation finishes before the exposure start time.

Again, in the above exemplary embodiment a case has been described in which the exposure start time is sent from the electronic cassette 32 to the console 42. However, the present invention is not limited thus. For example, an exposure finish time for radiation from the radiation source 130 may be sent from the console 42 to the electronic cassette 32 by wireless communications and, at the electronic cassette 32, the cassette control section 92 may start reading of charges from the radiation detector 60 at the exposure finish time, reading out the charges generated at the radiation detector 60 and generating image data representing a radiation image.

Anyway, the constitution of the RIS 10 described in the above exemplary embodiment (see FIG. 1), the constitution of the radiation image capturing system 18 (see FIG. 2 and FIG. 4) and the constitution of the electronic cassette 32 (see FIG. 3) are examples and obviously may be altered in accordance with circumstances within a scope not departing from the spirit of the present invention.

Moreover, the operational flow when photographing a radiation image described in the above exemplary embodiment (see FIG. 6) is an example and obviously may be altered in accordance with circumstances within a scope not departing from the spirit of the present invention.

Furthermore, the flow of the exposure timing determination processing described in the above exemplary embodiment (see FIG. 7) is an example and obviously may be altered in accordance with circumstances within a scope not departing from the spirit of the present invention.

A first aspect of the present invention is a radiation image capturing system including: a radiation source control device including a first timing component that measures time, and a control component that, when a time of the first timing component has reached a pre-specified exposure start time, controls a radiation source, which emits radiation, and performs control to cause radiation to be irradiated for a predetermined duration from the radiation source; and a radiation image capturing device including a second timing component that measures time, which is synchronized with the first timing component, a sensor portion that generates charges in accordance with irradiation of radiation and that is irradiated with the radiation from the radiation source, and a generation component that, after a time of the second timing component has passed through the predetermined duration from the exposure start time, reads out the charges generated at the sensor portion and generates image data representing a radiation image.

According to the invention of the first aspect, at the radiation source control device, time is measured by the first timing component, and when the time of the first timing component reaches the pre-specified exposure start time, the control component controls the radiation source which emits radiation and carries out control to cause radiation to be irradiated from the radiation source for the predetermined duration.

Meanwhile, at the radiation image capturing device, time is measured by the second timing component synchronously with the first timing component, and the generation component, after the time of the second timing component has gone through the predetermined duration from the exposure start time, reads out the charges generated at the sensor portion and generates the image data representing a radiation image.

Thus, according to the first aspect, synchronized times are measured at each of the radiation source control device and the radiation image capturing device, the radiation source control device causes radiation to be emitted for the predetermined duration from the radiation source when the pre-specified exposure start time is reached, and, after the predetermined duration has passed from the exposure start time, the radiation image capturing device reads the charges produced at the sensor portion and generates the image data representing a radiation image. Thus, exposure timings may be synchronized and radiation images assuredly photographed.

A second aspect of the present invention is the radiation image capturing system of the first aspect in which the times of the first timing component and the second timing component are synchronized by identical time information, which is received from outside.

A third aspect of the present invention is the radiation image capturing system of the first or second aspect in which the radiation image capturing device and the radiation source control device each further includes a communication component, the communication components performing wireless communications with one another, and the exposure start time is sent from one to the other of the radiation image capturing device and the radiation source control device by wireless communications.

A fourth aspect of the present invention is the radiation image capturing system of the third aspect in which the radiation image capturing device further includes a reset control component that performs control so as to repeat a reset operation which reads out and erases charges generated at the sensor portion, and a time at which the reset operation will finish is sent from the radiation image capturing device to the radiation source control device by wireless communications to serve as the exposure start time.

A fifth aspect of the present invention is the radiation image capturing system of the third or fourth aspect in which an exposure finish time of the radiation from the radiation source is sent from the radiation source control device to the radiation image capturing device by wireless communications, and when the exposure finish time is reached, the generation component reads out the charges generated at the sensor portion and generates the image data representing the radiation image.

A sixth aspect of the present invention is the radiation image capturing system of any of the first to fifth aspects in which the predetermined duration is altered in accordance with at least one of a radiation amount of the radiation irradiated from the radiation source, a location that is an object of photographing, and an image capturing mode.

A seventh aspect of the present invention is the radiation image capturing system of any of the first to sixth aspects in which at least one of the radiation source control device and the radiation image capturing device is plurally provided.

According to the present invention, synchronized times are respectively measured at a radiation source control device and a radiation image capturing device, and when a pre-specified exposure start time is reached, the radiation source control device causes radiation to be emitted for a predetermined duration from the radiation source, and after the predetermined duration has passed from the exposure start time, the radiation image capturing device reads charges generated at a sensor portion and generates image data representing a radiation image. Thus, an effect is provided in that exposure timings may be synchronized and radiation images assuredly photographed.

What is claimed is:

1. A radiation image capturing system comprising:
    a radiation source control device including
        a first timing component that measures time, and
        a control component that, when a time of the first timing component has reached a pre-specified exposure start time, controls a radiation source, which emits radiation, and performs control to cause radiation to be irradiated for a predetermined duration from the radiation source; and
    a radiation image capturing device including
        a second timing component that measures time, which is synchronized with the first timing component,
        a sensor portion that generates charges in accordance with irradiation of radiation and that is irradiated with the radiation from the radiation source, and
        a generation component that, after a time of the second timing component has passed through the predetermined duration from the exposure start time, reads out the charges generated at the sensor portion and generates image data representing a radiation image.

2. The radiation image capturing system according to claim 1, wherein the times of the first timing component and the second timing component are synchronized by identical time information, which is received from outside.

3. The radiation image capturing system according to claim 1, wherein the radiation image capturing device and the radiation source control device each further includes a communication component, the communication components performing wireless communications with one another, and
    the exposure start time is sent from one to the other of the radiation image capturing device and the radiation source control device by wireless communications.

4. The radiation image capturing system according to claim 3, wherein
    the radiation image capturing device further includes a reset control component that performs control so as to repeat a reset operation which reads out and erases charges generated at the sensor portion, and
    a time at which the reset operation will finish is sent from the radiation image capturing device to the radiation source control device by wireless communications to serve as the exposure start time.

5. The radiation image capturing system according to claim 3, wherein
    an exposure finish time of the radiation from the radiation source is sent from the radiation source control device to the radiation image capturing device by wireless communications, and
    when the exposure finish time is reached, the generation component reads out the charges generated at the sensor portion and generates the image data representing the radiation image.

6. The radiation image capturing system according to claim 1, wherein the predetermined duration is altered in accordance with at least one of a radiation amount of the radiation irradiated from the radiation source, a location that is an object of imaging, and an imaging mode.

7. The radiation image capturing system according to claim 1, wherein at least one of the radiation source control device and the radiation image capturing device is plurally provided.

8. A radiation image capturing method comprising:
    measuring time with a first timing component of a radiation source control device;
    when a time of the first timing component has reached a pre-specified exposure start time, controlling a radiation source, which emits radiation, with a control component of the radiation source control device and performing control to cause radiation to be irradiated for a predetermined duration from the radiation source;
    measuring time, synchronized with the first timing component, with a second timing component of a radiation image capturing device;
    generating charges in accordance with the irradiation of radiation from the radiation source, with a sensor portion of the radiation image capturing device; and
    after a time of the second timing component has passed through the predetermined duration from the exposure start time, reading out the charges generated at the sensor portion and generating image data representing a radiation image with a generation component of the radiation image capturing device.

9. The radiation image capturing method according to claim 8, wherein the times of the first timing component and the second timing component are synchronized with identical time information, which is received from outside.

10. The radiation image capturing method according to claim 8, wherein the exposure start time is sent from one to the other of the radiation image capturing device and the radiation source control device by wireless communications.

11. The radiation image capturing method according to claim 10, wherein a reset operation, which reads out and erases charges generated at the sensor portion, with a reset control component of the radiation image capturing device is repeatedly performed; and a time at which the reset operation will finish is sent from the radiation image capturing device to the radiation source control device by wireless communications to serve as the exposure start time.

12. The radiation image capturing method according to claim 10, wherein an exposure finish time of the radiation from the radiation source is sent from the radiation source control device to the radiation image capturing device by wireless communications; and when the exposure finish time is reached, the charges generated at the sensor portion are read out and the image data representing the radiation image are generated with the generation component.

13. The radiation image capturing method according to claim 8, wherein the predetermined duration is altered in accordance with at least one of a radiation amount of the radiation irradiated from the radiation source, a location that is an object of imaging, and an imaging mode.

* * * * *